(12) United States Patent  
Gerdts et al.

(10) Patent No.: US 8,114,057 B2
(45) Date of Patent: Feb. 14, 2012

(54) MEDICAL SYSTEMS INCLUDING A TELESCOPING SLEEVE AND RELATED COMPONENTS AND METHODS

(75) Inventors: Michael Gerdts, Big Lake, MN (US); Andrzej Malewicz, Minneapolis, MN (US); John R. Moberg, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 988 days.

(21) Appl. No.: 12/025,944

(22) Filed: Feb. 5, 2008

(65) Prior Publication Data
US 2008/0228258 A1 Sep. 18, 2008

Related U.S. Application Data

(60) Provisional application No. 60/888,224, filed on Feb. 5, 2007.

(51) Int. Cl.
*A61M 5/14* (2006.01)

(52) U.S. Cl. ...................................................... 604/256

(58) Field of Classification Search ............. 604/164.01, 604/164.1, 164.11, 165.01, 165.02, 171, 604/272, 264, 533, 534, 535, 536, 284, 167.03, 604/246, 167.01; 606/200, 108
See application file for complete search history.

(56) References Cited

U.S. PATENT DOCUMENTS

| | | | |
|---|---|---|---|
| 4,655,771 A | 4/1987 | Wallsten | |
| 4,848,343 A | 7/1989 | Wallsten et al. | |
| 4,990,151 A | 2/1991 | Wallsten | |
| 4,994,027 A * | 2/1991 | Farrell | 604/510 |
| 5,026,377 A | 6/1991 | Burton et al. | |
| 5,324,269 A | 6/1994 | Miraki | |
| 5,360,401 A | 11/1994 | Turnland | |
| 5,389,087 A | 2/1995 | Miraki | |
| 5,405,323 A | 4/1995 | Rogers et al. | |
| 5,458,605 A | 10/1995 | Klemm | |
| 5,484,444 A | 1/1996 | Braunschweiler et al. | |
| 5,507,768 A | 4/1996 | Lau et al. | |
| 5,533,968 A | 7/1996 | Muni et al. | |
| 5,662,616 A * | 9/1997 | Bousquet | 604/175 |
| 5,690,644 A | 11/1997 | Yurek et al. | |
| 5,709,703 A | 1/1998 | Lukie et al. | |
| 5,743,874 A | 4/1998 | Fischell et al. | |
| 5,782,855 A | 7/1998 | Lau et al. | |
| 5,843,028 A | 12/1998 | Weaver et al. | |
| 5,843,091 A | 12/1998 | Holsinger | |
| 5,921,971 A | 7/1999 | Agro et al. | |

(Continued)

FOREIGN PATENT DOCUMENTS

EP 0426407 5/1991

(Continued)

OTHER PUBLICATIONS

International Search Report and Written Opinion; PCT/US2008/053022; mailed Jul. 3, 2008.

*Primary Examiner* — Christopher D Koharski
(74) *Attorney, Agent, or Firm* — Seager, Tufte & Wickhem, LLC

(57) ABSTRACT

This invention relates to medical systems and related components and methods. In some embodiments, the systems include a sleeve configured to be disposed between an adaptor and a catheter assembly including an outer sheath surrounding an inner member.

27 Claims, 13 Drawing Sheets

U.S. PATENT DOCUMENTS

| | | | |
|---|---|---|---|
| 5,980,533 A | 11/1999 | Holman | |
| 6,007,522 A | 12/1999 | Agro et al. | |
| 6,059,752 A | 5/2000 | Segal | |
| 6,077,295 A | 6/2000 | Limon et al. | |
| 6,113,607 A | 9/2000 | Lau et al. | |
| 6,287,280 B1 * | 9/2001 | Lampropoulos et al. | 604/167.03 |
| 6,380,457 B1 | 4/2002 | Yurek et al. | |
| 6,592,549 B2 | 7/2003 | Gerdts et al. | |
| 6,676,900 B1 * | 1/2004 | Divino et al. | 422/45 |
| 2004/0147877 A1 * | 7/2004 | Heuser | 604/165.02 |
| 2004/0220519 A1 | 11/2004 | Wulfman et al. | |
| 2005/0027345 A1 | 2/2005 | Horan et al. | |
| 2005/0080476 A1 | 4/2005 | Gunderson et al. | |
| 2006/0074477 A1 | 4/2006 | Berthiaume et al. | |
| 2006/0190069 A1 | 8/2006 | Baker-Janis et al. | |

FOREIGN PATENT DOCUMENTS

| | | |
|---|---|---|
| EP | 050686 | 9/1992 |
| EP | 0696447 | 2/1996 |
| EP | 0875262 | 11/1998 |
| WO | 9949808 | 10/1999 |
| WO | 0069498 | 11/2000 |
| WO | WO 2004/071352 | 8/2004 |
| WO | 2005112824 | 12/2005 |
| WO | 2008097949 | 8/2008 |

* cited by examiner

MEDICAL SYSTEMS INCLUDING A TELESCOPING SLEEVE AND RELATED COMPONENTS AND METHODS

CROSS-REFERENCE TO RELATED APPLICATIONS

This application claims the benefit of U.S. Provisional Application Ser. No. 60/888,224, filed on Feb. 5, 2007. The above-noted provisional application is incorporated by reference in its entirety.

TECHNICAL FIELD

This invention relates to medical systems and related components and methods.

BACKGROUND

Devices are known for delivering implantable endoprostheses, such as stents, into a body vessel. Devices of this kind often include a proximal portion that remains external to the body vessel during use and a distal portion that is inserted into the body vessel (e.g., through an incision). The proximal portion typically provides for manipulation of the device during use. The distal portion often includes an outer sheath slidably positioned about an inner member with an endoprosthesis disposed therebetween. Generally, the distal portion of the device is advanced through the body vessel to a treatment site (e.g., a stenosis or aneurysm). The outer sheath can then be retracted to allow the endoprosthesis to expand to engage a wall of the body vessel at the treatment site. Thereafter, the device is removed leaving the endoprosthesis engaged with the body vessel.

SUMMARY

In one aspect of the invention, a system includes an adaptor defining a lumen configured to receive a portion of a catheter assembly having an inner member at least partially surrounded by an outer sheath. The system also includes a sleeve configured to be disposed between the outer sheath of the catheter assembly and the adaptor when the catheter assembly is disposed in the lumen of the adaptor.

In another aspect of the invention, a system includes a valve defining a lumen. The valve is configured to be placed in a first position in which the lumen has a first diameter and a second position in which the lumen has a second diameter that is smaller than the first diameter. The system further includes a sleeve configured to be disposed within the lumen of the valve. The sleeve is configured so that a catheter assembly having an inner tubular member and an outer tubular member at least partially surrounding the inner tubular member can extend through the sleeve. The sleeve is configured so that a level of friction between the sleeve and the outer tubular member, when the catheter assembly extends through the sleeve and the sleeve is disposed in the lumen of the valve, is substantially constant in the first position and the second position.

In a further aspect of the invention, a system includes a valve and a sleeve defining a lumen and being configured to be disposed within the valve so that a substantially liquid-tight seal can be created between the valve and the sleeve. The sleeve is configured so that a catheter assembly including an inner tubular member and an outer tubular member at least partially surrounding the inner tubular member can be disposed within the lumen of the sleeve. The sleeve includes an inner layer and an outer layer, and the inner layer has a coefficient of friction of about 0.25 or less.

In an additional aspect of the invention, a method includes disposing a sleeve between a valve and an outer sheath of a catheter assembly. The catheter assembly includes an inner member extending within a lumen of the outer sheath. The method also includes compressing the valve around the sleeve and retracting the outer sheath of the catheter assembly relative to the valve.

Embodiments can include one or more of the following features.

In some embodiments, the sleeve is substantially radially incompressible.

In some embodiments, the sleeve is formed of one or more materials having a tensile strength of at least about 63 MPa, and the sleeve has a wall thickness of at least about 0.002 inch.

In some embodiments, a distal portion of the sleeve is configured to be disposed between the outer sheath of the catheter assembly and the adaptor, and a proximal portion of the sleeve is configured to be positioned proximal to the adaptor.

In some embodiments, the proximal portion of the sleeve has a first outer diameter and the distal portion of the sleeve has a second outer diameter. The first outer diameter is greater than the second outer diameter.

In some embodiments, a proximal end region of the sleeve is secured to a handle to which the inner member of the catheter assembly is secured.

In some embodiments, the sleeve is configured to extend from the adaptor to a distal end of a handle to which the inner member of the catheter assembly is secured.

In some embodiments, the sleeve is a telescoping sleeve.

In some embodiments, a proximal end region of the telescoping sleeve is secured to a handle to which the inner member of the catheter assembly is secured.

In some embodiments, the adaptor includes a valve that can be tightened around the sleeve when the sleeve is disposed between the adaptor and the outer sheath of the catheter assembly.

In some embodiments, the sleeve is configured so that a friction level between the sleeve and the outer sheath of the catheter assembly remains substantially constant as the valve is tightened around the sleeve.

In some embodiments, the sleeve includes one or more rigid materials.

In some embodiments, the sleeve includes one or more materials having a tensile strength of at least about 63 MPa.

In some embodiments, the sleeve includes one or more metals or alloys (e.g., stainless steel).

In some embodiments, the sleeve includes an inner layer and an outer layer.

In some embodiments, the outer layer is formed of one or more materials having a tensile strength of at least about 63 MPa.

In some embodiments, the inner layer includes one or more lubricious materials (e.g., silicone, PTFE, hydrophilic coatings, etc.).

In some embodiments, the inner layer has a coefficient of friction of about 0.25 or less.

In some embodiments, the sleeve has an inner diameter and the outer sheath of the catheter assembly has an outer diameter. The inner diameter of the sleeve is no greater than about 0.003 inch greater than (e.g., about 0.0005 inch to about 0.003 inch greater than) the outer diameter of the outer sheath of the catheter assembly.

In some embodiments, the system further includes a guide catheter secured to a distal end region of the adaptor.

In some embodiments, the valve includes a resilient o-ring.

In some embodiments, the valve is a Touhy Borst valve.

In some embodiments, the system further includes an introducer sheath, and the valve is disposed within the introducer sheath.

In some embodiments, the valve is a membrane disposed within the introducer sheath, and the membrane has intersecting slits through which a catheter assembly can be inserted.

In some embodiments, the sleeve is configured to extend from the introducer sheath to a distal end of a handle to which the inner member of the catheter assembly is secured.

In some embodiments, the valve is disposed within an adaptor that is adapted to be secured to a guide catheter.

In some embodiments, the valve is disposed within an introducer sheath.

In some embodiments, the method further includes retracting the outer sheath relative to the inner member.

In some embodiments, the inner member and the outer sheath are configured so that an implantable medical endoprosthesis can be disposed therebetween.

In some embodiments, the compressed portion of the valve defines a central lumen, and the valve is configured to be placed in a first uncompressed position in which the central lumen has a first diameter and a second compressed position in which the central lumen has a second diameter. The second diameter is smaller than the first diameter.

In some embodiments, an implantable medical endoprosthesis initially disposed between the outer sheath and the inner member expands as the outer sheath is retracted relative to the inner member.

In some embodiments, the method further includes securing an adaptor comprising the valve to a guide catheter.

Embodiments can include one or more of the following advantages.

In certain embodiments, the sleeve includes an inner lubricious layer. The inner lubricious layer of the sleeve can reduce the level of friction between the sleeve and the outer sheath of the catheter assembly during use. In some instances, due to the reduced level of friction between the sleeve and the outer sheath of the catheter assembly, the accuracy with which an implantable medical endoprosthesis (e.g., a self-expanding stent) is deployed within a body vessel of a patient can be improved.

In some embodiments, the sleeve is substantially radially incompressible. This can prevent a substantial increase in friction between the sleeve and the outer sheath of the catheter assembly during use. For example, this arrangement can prevent a substantial increase in friction between the sleeve and the outer sheath of the catheter assembly as a result of the valve (e.g., the valve of the adaptor) being overly tightened (e.g., overly compressed) by the user of the system.

In certain embodiments, the sleeve is configured to extend between the proximal end of the valve (e.g., the proximal end of the valve of the adaptor) and the distal end of the handle to which the inner member of the catheter assembly is attached. This configuration can inhibit the handle and inner member from moving longitudinally relative to the adaptor during use. As a result, the accuracy with which an implantable medical endoprosthesis (e.g., a self-expanding stent) is delivered within a body vessel using the catheter assembly can be improved.

In some embodiments, the sleeve has a telescoping configuration that permits the length of the sleeve to be adjusted to substantially equal the length of the catheter assembly exposed between the proximal end of the valve (e.g., the proximal end of the valve of the adaptor) and the distal end of the handle. As a result, the sleeve can be used for various treatments requiring different longitudinal positioning of the catheter assembly relative to the valve or the adaptor.

In certain embodiments, the sleeve is configured to be disposed between the valve and the outer sheath of the catheter assembly, at a location outside the patient. As a result, a low profile of the portion of the stent delivery system inserted into the patient can be maintained.

Other aspects, features, and advantages are in the description, drawings, and claims.

DETAILED DESCRIPTION

In certain aspects of the invention, a system includes a valve (e.g., an adaptor including a valve) configured so that a catheter assembly including an inner member and a retractable outer sheath surrounding the inner member can extend through the valve. The system also includes a sleeve (e.g., a telescoping sleeve) configured to be disposed between the valve and the outer sheath of the catheter assembly when the catheter assembly is disposed within the valve. In some embodiments, the sleeve includes (e.g., is formed of) one or more substantially incompressible materials. In certain embodiments, the sleeve includes an inner layer and an outer layer, and the inner layer includes (e.g., is formed of) one or more lubricious materials.

Figure 1:
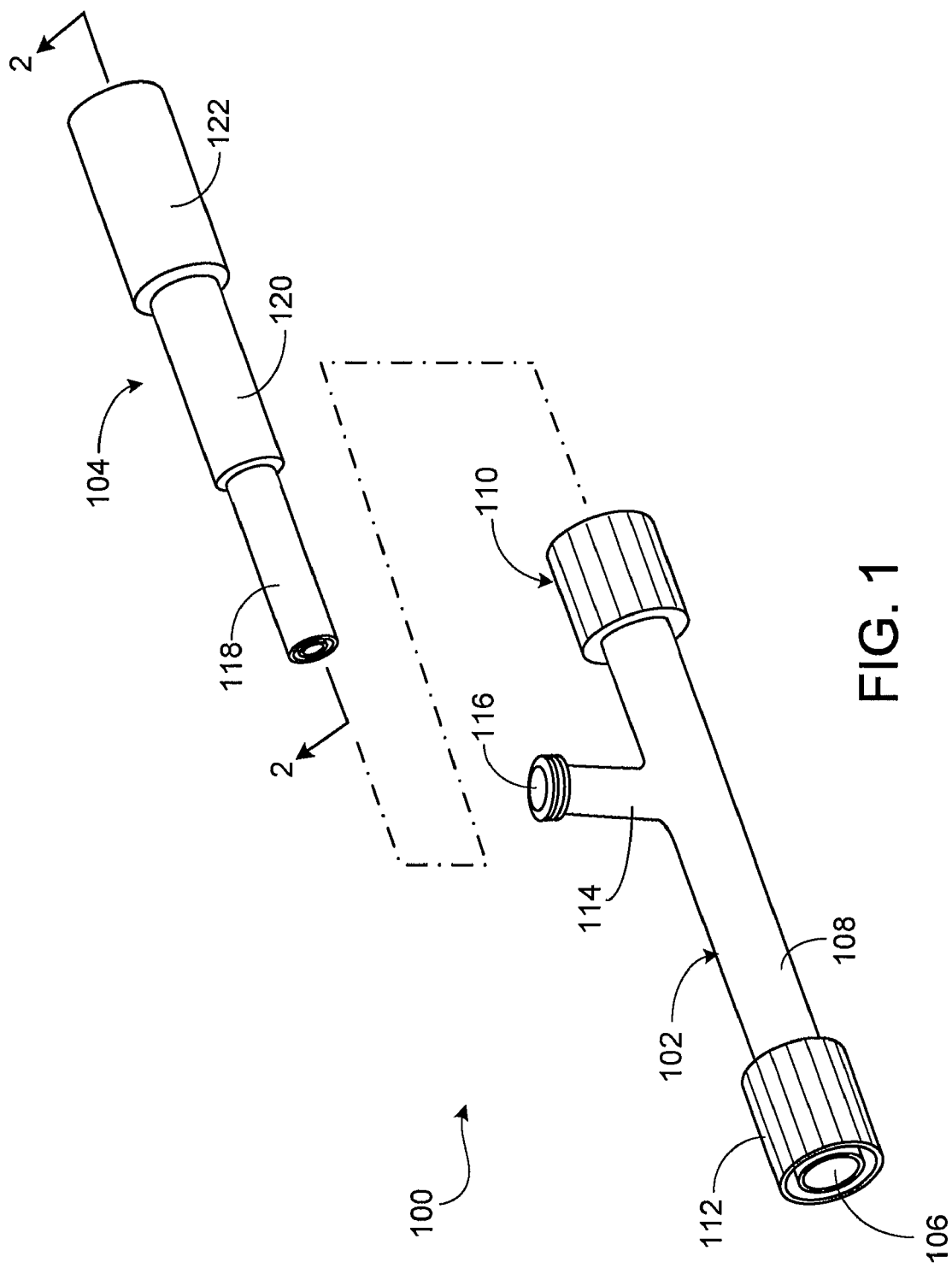
FIG. 1 is a perspective, partially exploded view of an adaptor system including a Y-adaptor and a telescoping sleeve.

Referring to FIG. 1, an adaptor system 100 includes a Y-adaptor 102 and a telescoping sleeve 104 that can be partially inserted into a lumen 106 extending through a housing 108 of Y-adaptor 102. A Touhy Borst valve 110 is secured to a proximal end region of housing 108, and a luer-lock fitting 112 is secured to a distal end region of housing 108. A tubular branch 114 extends laterally from housing 108 and includes a branch lumen 116 in fluid communication with lumen 106 of housing 108. Thus, during use, fluid can be introduced into lumen 106 of housing 108 via branch lumen 116 of tubular branch 114 (e.g., by connecting a syringe to tubular branch 114 and using the syringe to force the fluid into branch lumen 116).

Telescoping sleeve 104 is a collapsible assembly that includes first, second, and third tubes 118, 120, 122. First tube 118 has an outer diameter that is slightly less than (e.g., about 0.0005 inch to about 0.002 inch less than) an inner diameter of second tube 120, and second tube 120 has an outer diameter that is slightly less than (e.g., about 0.0005 inch to about 0.002 inch less than) an inner diameter of third tube 122. Thus, first tube 118 can slide within second tube 120, and second tube 120 can slide within third tube 122.

Figure 2:
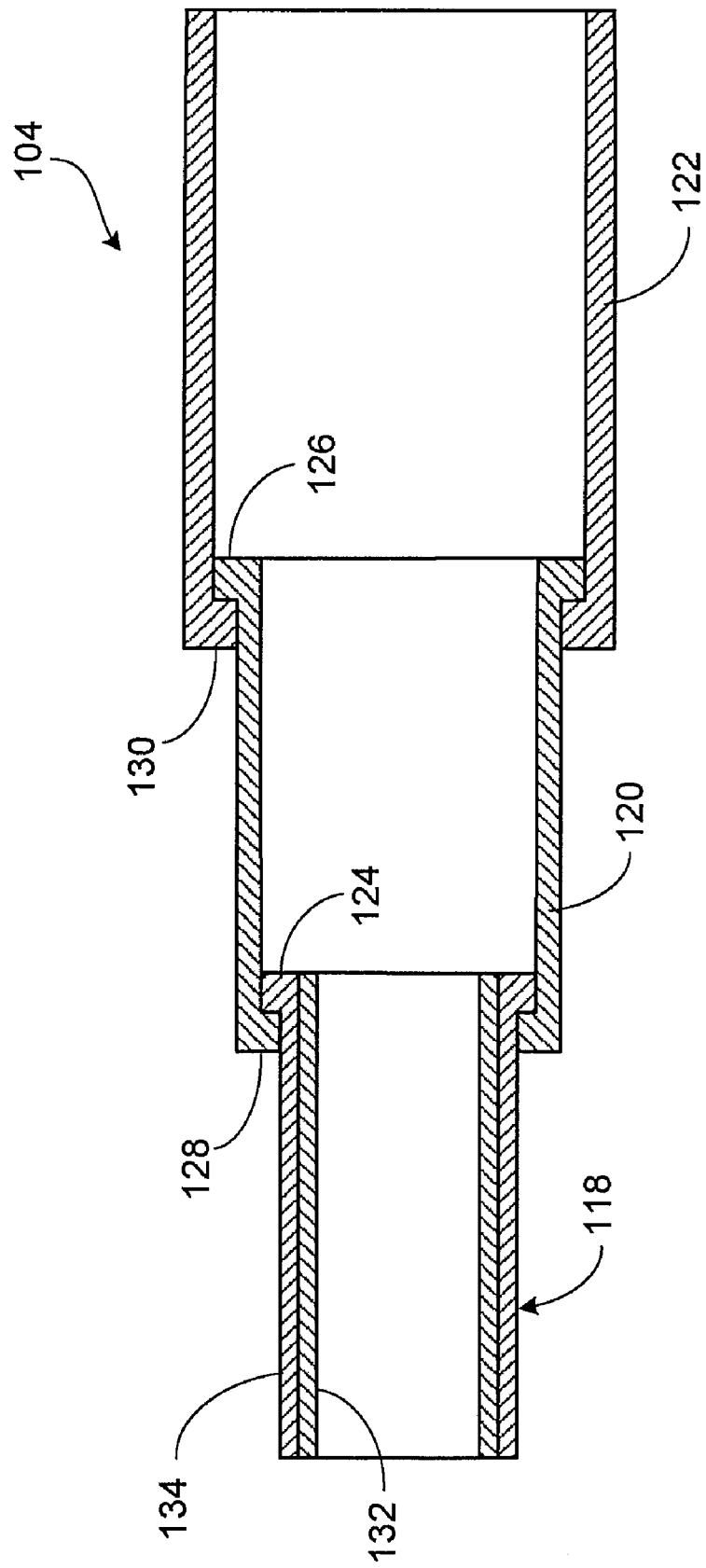
FIG. 2 is a cross-sectional view of the telescoping sleeve of FIG. 1.

Referring to FIG. 2, first and second tubes 118, 120 of telescoping sleeve 104 include proximal stops 124, 126 that project radially outward from the outer surfaces of first and second tubes 118, 120. Second and third tubes 120, 122 include distal stops 128, 130 that project radially inward from the inner surfaces of second and third tubes 120, 122. Thus, when telescoping sleeve 104 is fully expanded, as shown in FIG. 2, proximal stop 124 of first tube 118 abuts distal stop 128 of second tube 120, and proximal stop 126 of second tube 120 abuts distal stop 130 of third tube 122. This arrangement prevents first, second, and third tubes 118, 120, 122 from becoming separated from one another when telescoping sleeve 104 is expanded. In certain embodiments, proximal stops 124, 126 of first and second tubes 118, 120 have outer diameters that are about 0.0005 inch to about 0.002 inch less than the inner diameters of second and third tubes 120, 122, respectively. In some embodiments, distal stops 128, 130 of second and third tubes 120, 122 have inner diameters that are about 0.0005 inch to about 0.002 inch greater than the outer diameters of first and second tubes 120, 122, respectively. This arrangement can provide resistance to the expansion and contraction of telescoping sleeve 104. Such an arrangement can, for example, help to prevent inadvertent expansion and contraction of telescoping sleeve 104 during use.

Still referring to FIG. 2, first tube 118 of telescoping sleeve 104 includes an inner layer 132 and an outer layer 134. Inner layer 132 can include (e.g., can be formed of) one or more lubricious materials. Inner layer 132 can, for example, have a lower coefficient of friction than outer layer 134. In some embodiments, inner layer 132 (e.g., the material(s) from which inner layer 134 is formed) has a coefficient of friction of about 0.25 or less (e.g., about 0.05 to about 0.1). Examples of materials from which inner layer 132 can be formed include silicone, polytetrafluoroethylene (PTFE), and hydrophilic coatings. Outer layer 134 can include (e.g., can be formed of) any of various rigid materials. The rigidity of outer layer 134 can prevent first tube 118 of telescoping sleeve 104 from being radially deformed as a result of inward forces applied to the outer surface of first tube 118 by valve 110 during use, as discussed in more detail below. In some embodiments, the material(s) from which outer layer 134 is formed has/have a tensile strength of at least about 63 MPa (e.g., at least about 100 MPa, at least about 150 MPa, at least about 200 MPa, at least about 400 MPa, at least about 800 MPa, about 100 MPa to about 1200 MPa, about 400 MPa to about 1200 MPa). Examples of materials from which outer layer 134 can be formed include stainless steel, polycarbonate, and acrylonitrile butadiene styrene (ABS). Outer layer 134 can have a wall thickness of about 0.002 inch or greater (e.g., about 0.003 inch or greater, about 0.002 inch to about 0.004 inch, about 0.003 inch to about 0.006 inch).

In some embodiments, second and third tubes 120, 122 include (e.g., are formed of) one or more rigid materials, such as stainless steel, polycarbonate, and/or acrylonitrile butadiene styrene (ABS). Alternatively or additionally, second and third tubes 120, 122 can include more flexible materials. In certain embodiments, for example, second and third tubes 120, 122 include one or more relatively flexible polymeric materials, such as braided polyimide, polyetheretherketone (PEEK), and/or nylon (e.g., nylon 12).

Figure 3A:
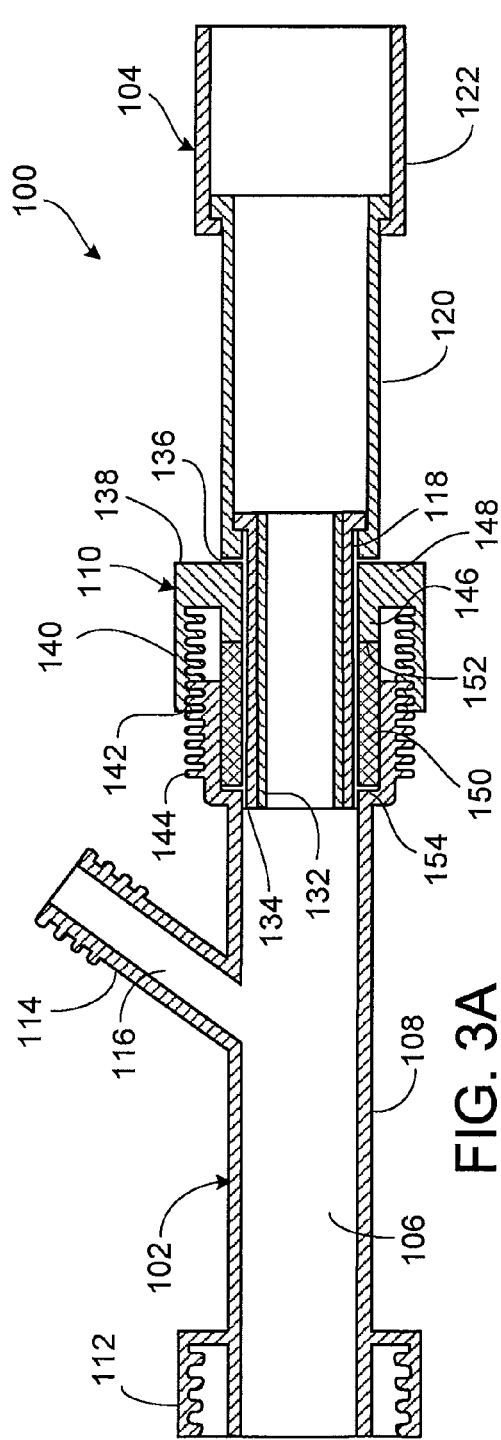
FIGS. 3A and 3B are cross-sectional views of the adaptor system of FIG. 1 in an unsealed configuration and in a sealed configuration, respectively.

During use of adaptor system 100, first tube 118 of telescoping sleeve 104 is inserted into Y-adaptor 102, as shown in FIG. 3A. First tube 118, when fully inserted into Y-adaptor 102 extends slightly past valve 110. In this position, a distal end 136 of second tube 120, which has an outer diameter that is greater than an inner diameter of a proximal end 138 of valve 110, abuts proximal end 138 of valve 110, preventing telescoping sleeve 104 from being further inserted into Y-adaptor 102.

Telescoping sleeve 104 can be provided in any of various sizes depending on the size of the Y-adaptor and catheter assembly with which it is to be used. In some embodiments, first tube 118 of telescoping sleeve 104 has an inner diameter of about 0.0405 inch to about 0.095 inch (e.g., about 0.0535 inch to about 0.069 inch). First tube 118 can have an outer diameter of about 0.0425 inch to about 0.111 inch (e.g., about 0.0555 inch to about 0.075 inch). In some embodiments, the smallest inner diameter of telescoping sleeve 104 (e.g., the inner diameter of first tube 118 of telescoping sleeve 104) is at most about 0.003 inch greater than (e.g., about 0.0005 inch to about 0.003 inch greater than) the outer diameter of an outer sheath of a catheter assembly with which adaptor system 100 is used. As a result, a substantially fluid-tight seal can be created between the inner surface of first tube 118 of telescoping sleeve 104 and the outer surface of the outer sheath of the catheter assembly when the catheter assembly is disposed within telescoping sleeve 104 during use.

Figure 3B:
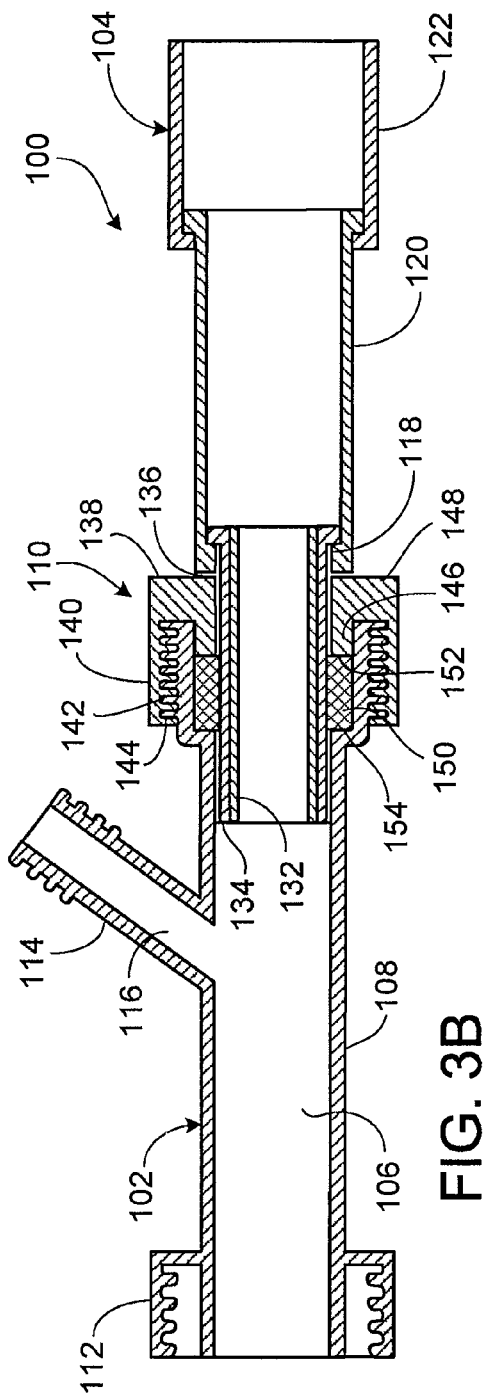

Still referring to FIG. 3A, valve 110 of Y-adaptor 102 includes a threaded fitting 140 that is secured to housing 108. Fitting 140 includes threads 142 that extend inwardly from an inner surface of fitting 140 and matingly engage threads 144 extending from an outer surface of housing 108. An annular portion 146 of fitting 140 extends distally from a proximal end portion 148 of fitting 140 and is spaced radially inward from the threaded portion of fitting 140. A compressible O-ring 150 is disposed between a distal end 152 of annular portion 146 and a radially inward projecting surface 154 of housing 108. As fitting 140 is rotated in a clockwise direction (as viewed from the proximal end of Y-adaptor 102), the engagement of threads 142 of fitting 140 and threads 144 of housing 108 cause fitting 140 to move distally along housing 108. As a result, O-ring 150 is compressed between annular portion 146 of fitting 140 and radially inward projecting surface 154 of housing 108, which causes O-ring 150 to bulge inward and contact the outer surface of first tube 118 of telescoping sleeve 104, as shown in FIG. 3B. Upon rotating fitting 140 a sufficient amount, a fluid-tight seal is created between the inner surface of O-ring 150 and the outer surface of first tube 118.

Due to the rigidity of outer layer 134 of first tube 118 of telescoping sleeve 104, first tube 118 is substantially prevented from being compressed inwardly as O-ring 150 bulges radially inward against the outer surface of first tube 118. As a result, a fluid-tight seal can be created between O-ring 150 and first tube 118 without altering the inner diameter of first tube 118. This arrangement can help to reduce frictional forces acting on an outer sheath of a catheter assembly disposed within Y-adaptor 102 as the outer sheath is retracted relative to first tube 118. In addition, this arrangement can help to ensure a consistent level of friction between the outer sheath of the catheter assembly and first tube 118 of telescoping sleeve 104 independent of the degree to which valve 110 is tightened during use.

Figure 4:
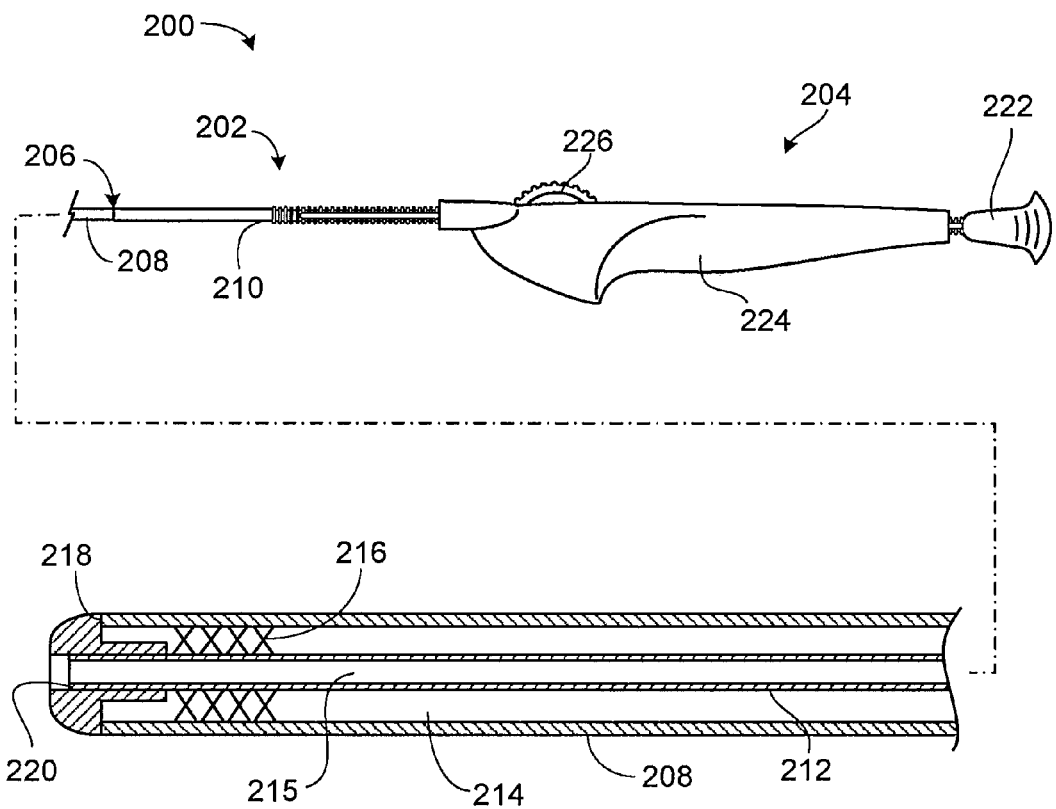
FIG. 4 illustrates a stent delivery system that can be used with the adaptor system of FIG. 1, with a distal portion of the catheter assembly of the stent delivery system shown in cross-section.

FIG. 4 illustrates a stent delivery system 200 that can be used with adaptor system 100. As shown in FIG. 4, stent delivery system 200 includes a catheter assembly 202 and a handle assembly 204. Catheter assembly 202 includes an outer tubular assembly 206 having an outer sheath 208 secured in its proximal end region to a tubular rack 210. Catheter assembly 202 also includes an inner tubular member 212 extending through a lumen 214 formed by outer tubular assembly 206. A guide wire lumen 215 extends through inner tubular member 212. A self-expanding stent 216 is disposed between outer sheath 208 and inner tubular member 212, near distal ends 218, 220 of outer sheath 208 and inner tubular member 212. A pull grip 222 is provided on a proximal end region of tubular rack 210. A proximal portion of catheter assembly 202 extends within a housing 224 of handle assembly 204. Inner tubular member 212 is secured to an inner surface of housing 224.

Handle assembly 204 includes a rotatable knob 226 that is rotatably fixed to housing 224 and is engaged (e.g., by a gear) with tubular rack 210. Outer sheath 208 can be retracted proximally relative to inner tubular member 212 by rotating rotatable knob 226 in a clockwise direction (in the view illustrated in FIG. 4) and/or by pulling proximally on pull grip 222.

Figure 5A:
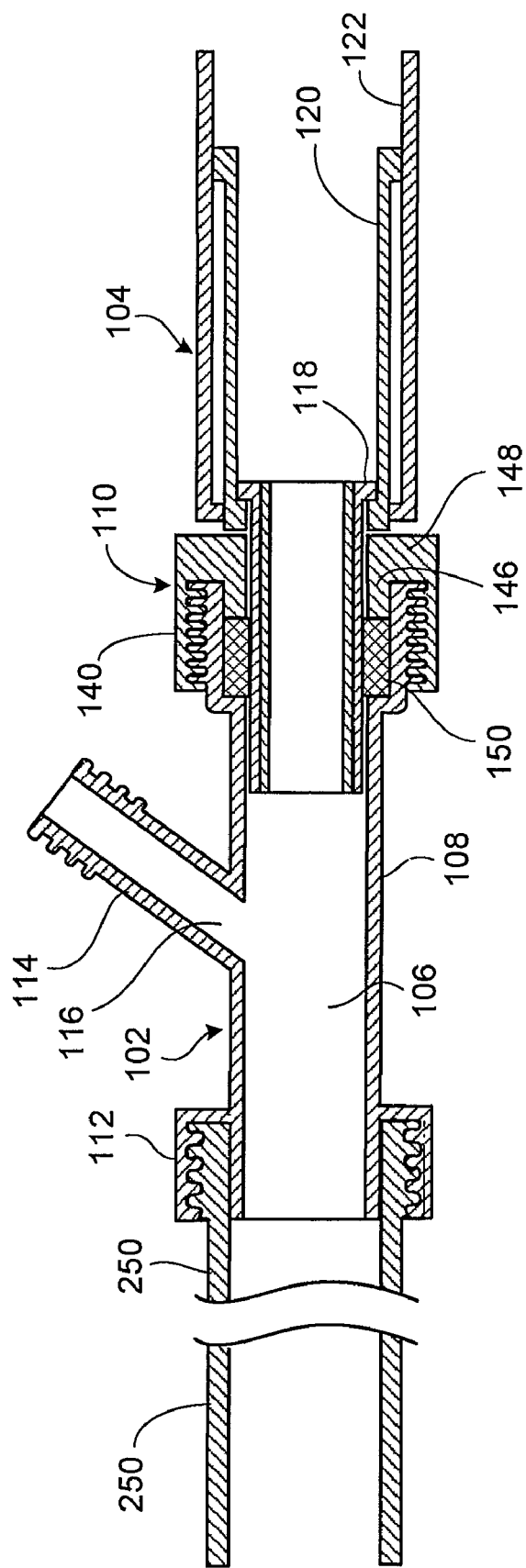
FIGS. 5A-5E illustrate a method of using the adaptor system of FIG. 1.

FIGS. 5A-5E illustrate a method of using adaptor system 100 to aid in the delivery and deployment of stent 216 using stent delivery system 200 (shown in FIG. 4). Referring to FIG. 5A, prior to use, first tube 118 of telescoping sleeve 104 is inserted into Y-adaptor 102 and valve 110 is tightened around first tube 118 to create a fluid-tight seal between O-ring 150 of valve 110 and first tube 118. At this point, telescoping sleeve 104 is in a contracted or collapsed configuration. In addition, a guide catheter 250 is secured to luer-lock fitting 112 at the distal end of Y-adaptor 102.

Figure 5B:
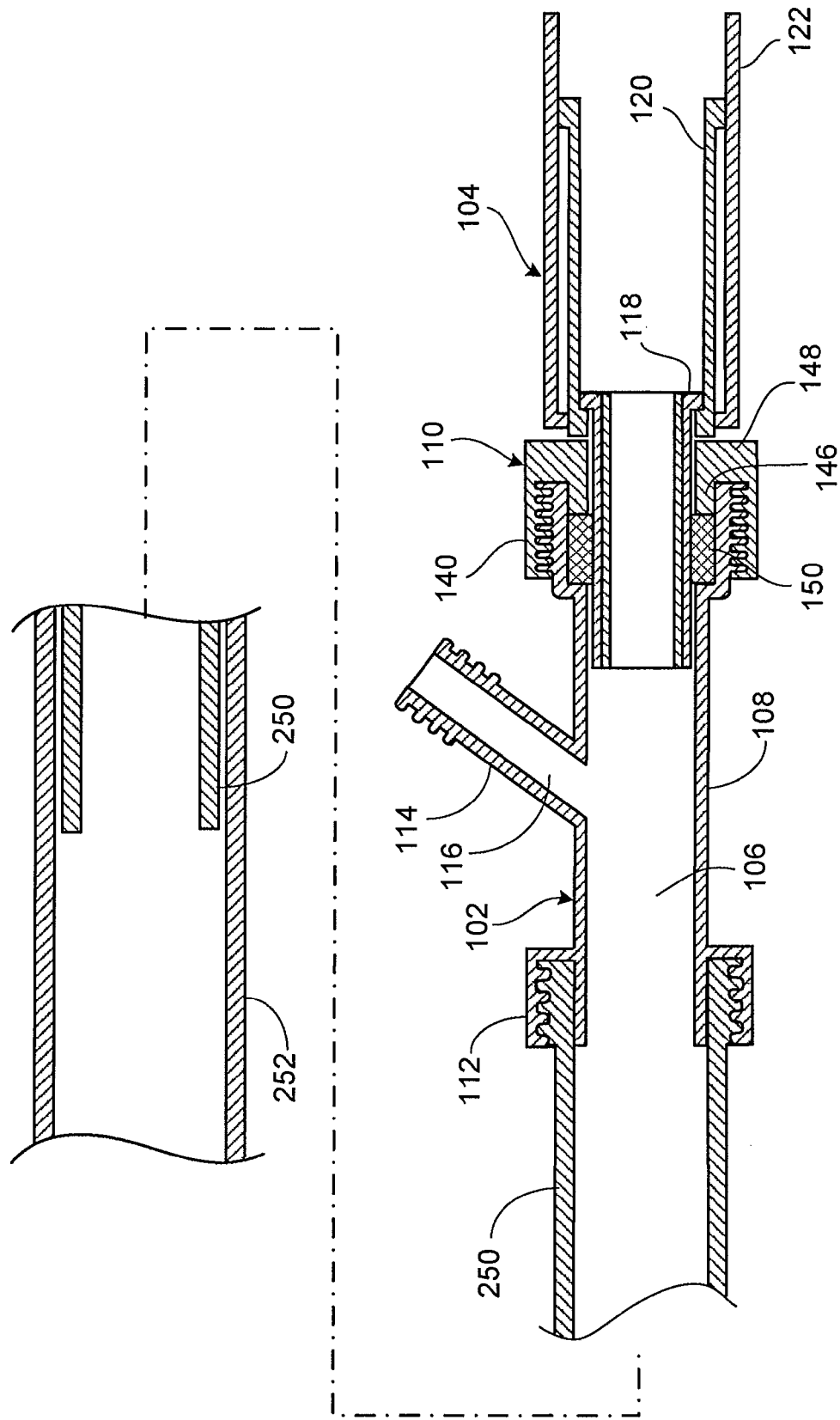

Referring to FIG. 5B, guide catheter 250 is subsequently inserted into a blood vessel 252 of a patient. Guide catheter 250 can be positioned as desired by the user within blood vessel 252 while Y-adaptor 102 remains outside the patient.

Figure 5C:
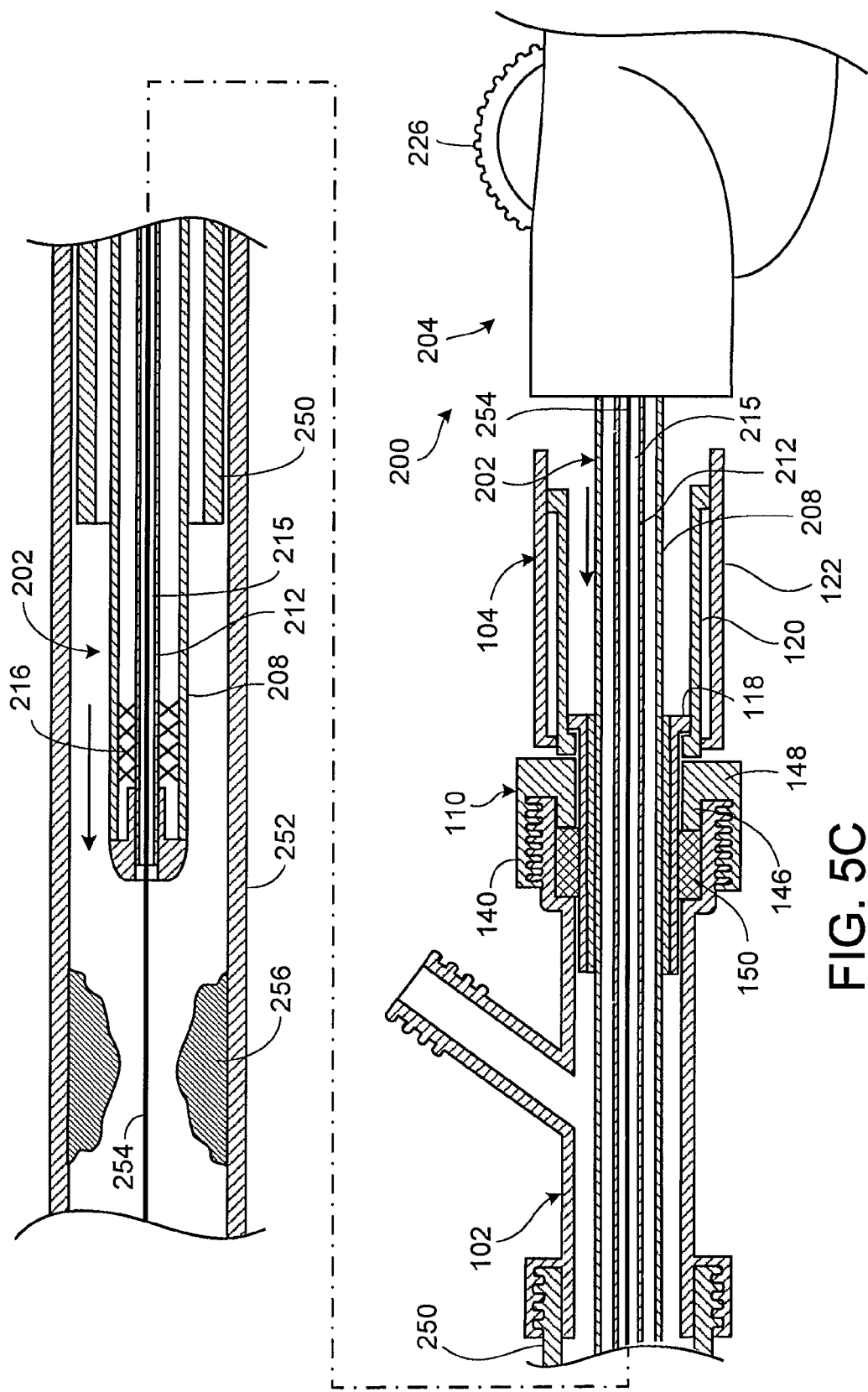

Referring to FIG. 5C, after positioning guide catheter 250 as desired within blood vessel 252, a guide wire 254 and catheter assembly 202 of stent delivery system 200 are inserted into blood vessel 252 via telescoping sleeve 104, Y-adaptor 102, and guide catheter 250. For example, guide wire 254 can first be inserted into blood vessel 252, and then catheter assembly 202 can be introduced into blood vessel 252 over guide wire 254 such that guide wire 254 becomes disposed within guide wire lumen 215 of inner tubular member 212. Outer sheath 208 of catheter assembly 202 and first tube 118 of telescoping sleeve 104 are configured so that, when catheter assembly 202 is disposed within first tube 118 of telescoping sleeve 104, a fluid-tight seal is created between the inner surface of first tube 118 and the outer surface of outer sheath 208. In some embodiments, for example, outer sheath 208 has an outer diameter that is no more than about 0.003 inch (e.g., about 0.0005 inch to about 0.003 inch) less than the inner diameter of first tube 118. In certain embodiments, outer sheath 208 has an outer diameter of about 0.040 inch to about 0.092 inch (e.g., about 0.053 inch to about 0.066 inch). A distal portion of catheter assembly 202 is navigated through blood vessel 252 and toward an occluded region 256 of blood vessel 252 by passing catheter assembly 202 over guide wire 254. While navigating catheter assembly 202 through blood vessel 252, the substantially fluid-tight seals between the inner surface of O-ring 150 and the outer surface of first tube 118 and between the outer surface of outer sheath 208 and the inner surface of first tube 118 can inhibit blood from leaking proximally through Y-adaptor 102. At the same time, lubricious inner layer 132 of first tube 118 helps to reduce friction between outer sheath 208 and first tube 118, which increases the ease with which the user can pass catheter assembly 202 through telescoping sleeve 104.

Figure 5D:
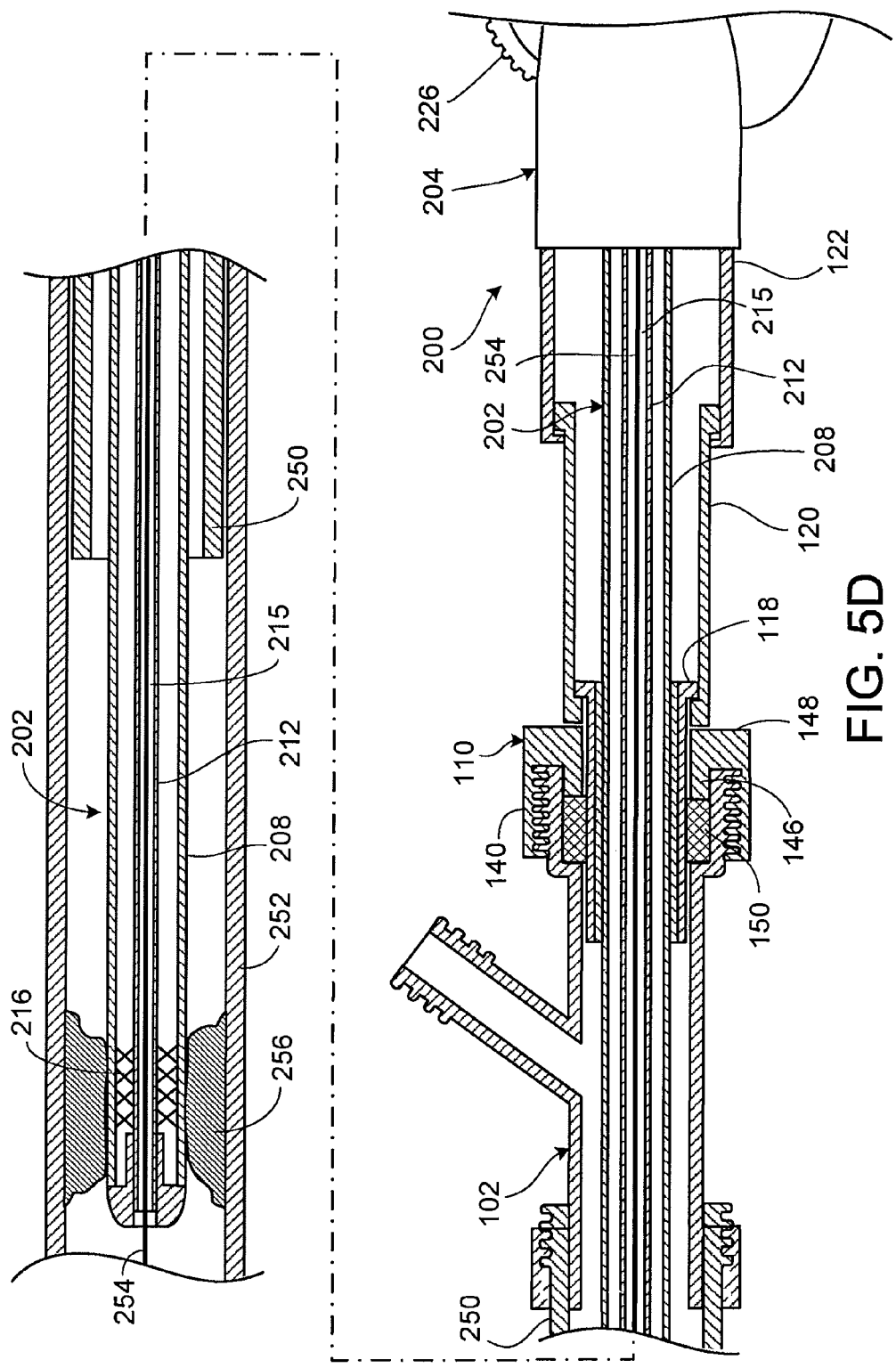

Catheter assembly 202 is navigated through blood vessel 252 until the stent-carrying portion of catheter assembly 202 is positioned within occluded region 256, as shown in FIG. 5D. Fluoroscopy or any of various other imaging techniques can be used to help the user position the stent-carrying portion of catheter assembly 202 within occluded region 256. After positioning the stent-carrying portion of catheter assembly 202 within occluded region 256, the user longitudinally expands telescoping sleeve 104 such that the proximal end of telescoping sleeve 104 abuts the distal end of handle assembly 204. Because telescoping sleeve 104 extends along the portion of catheter assembly 202 between handle assembly 204 and Y-adaptor 102, that portion of catheter assembly 202 can be inhibited from bowing or arching outward (e.g., transverse to the longitudinal axis of telescoping sleeve 104) during the remainder of the stent deployment procedure. This can help to improve the accuracy with which stent 216 is deployed. The friction between first, second, and third tubes 118, 120, 122 of telescoping sleeve 104 when in this expanded position can also help to inhibit handle assembly 204 from moving distally relative to Y-adaptor 102 during stent deployment, which can further improve the accuracy with which stent 216 is deployed.

Figure 5E:
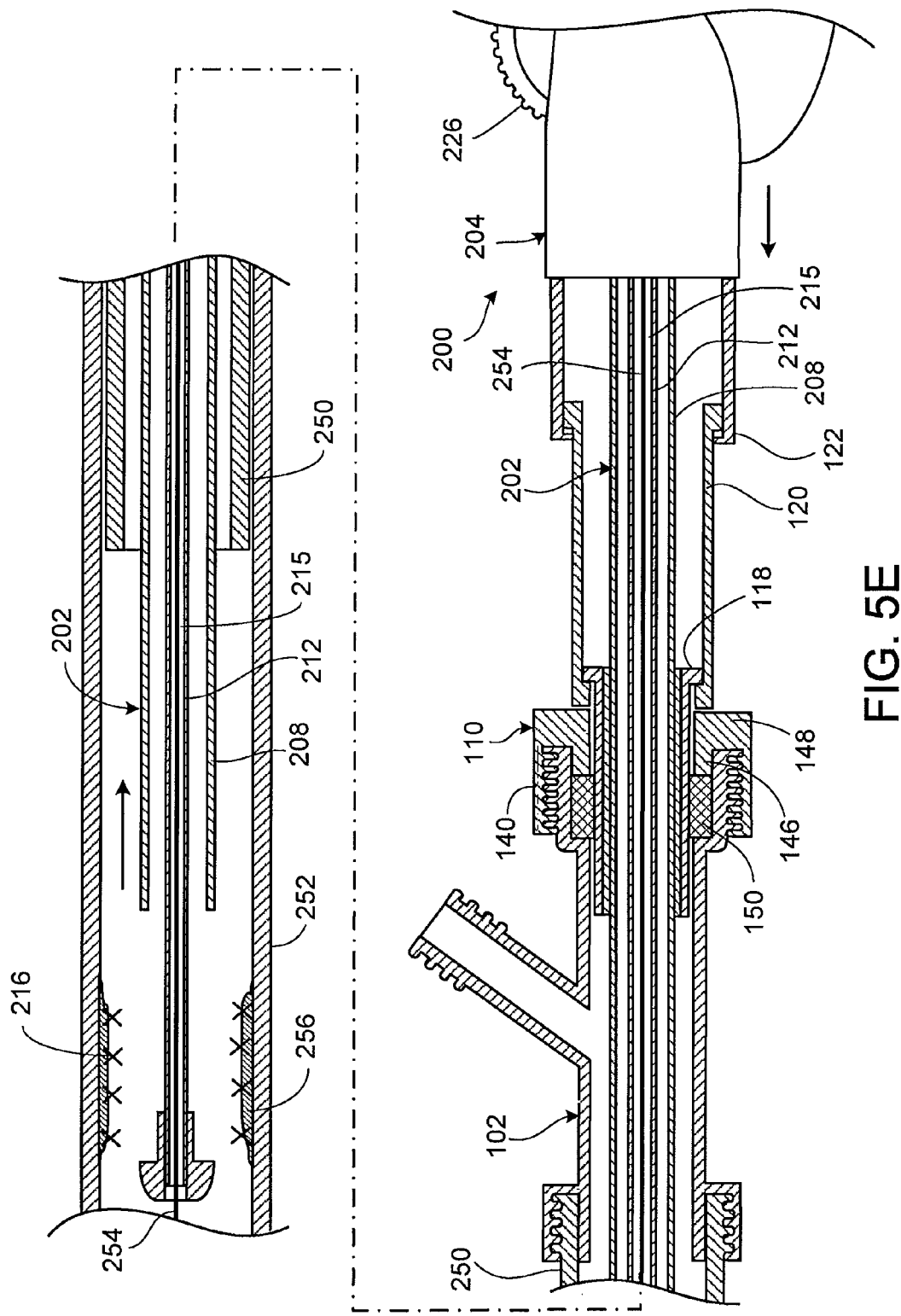

Referring to FIG. 5E, after the stent-carrying portion of catheter assembly 202 has been positioned within occluded region 256 and telescoping sleeve 104 has been longitudinally expanded to inhibit distal movement of stent delivery system 200 relative to adaptor system 100, outer sheath 208 is retracted proximally beyond stent 216, allowing stent 216 to self-expand within occluded region 256 and contact a wall of body vessel 252. Outer sheath 208 can, for example, be retracted by rotating rotatable knob 226 in a clockwise direction (in the view illustrated in FIG. 5E) and/or by pulling pull grip 222 in the proximal direction. Due to lubricious inner layer 132 of first tube 118 of telescoping sleeve 104, outer sheath 208 and first tube 118 experience relatively low levels of friction during retraction of outer sheath 208. As a result, the user is able to retract outer sheath 208 relatively easily. The low levels of friction that occur between outer sheath 208 and first tube 118 can also improve the accuracy with which stent 216 is deployed within blood vessel 252. In addition, expanded telescoping sleeve 104 can improve the accuracy with which stent 216 is deployed within blood vessel 252 because the user is less likely to inadvertently move handle assembly 204 of stent delivery system 200 while retracting outer sheath 208. Furthermore, expanded telescoping sleeve 104 can inhibit the portion of catheter assembly 202 exposed between handle assembly 204 and Y-adaptor 102 from bowing outward during deployment of stent 216, which can improve the accuracy with which stent 216 is deployed within blood vessel 252.

After deploying stent 216, stent delivery system 200, guide wire 254, and guide catheter 250 are withdrawn from blood vessel 252, leaving stent 216 implanted in blood vessel 252.

While certain embodiments have been described, other embodiments are possible.

As an example, while telescoping sleeve 104 has been described as including three telescoping tubes, telescoping sleeve 104 can alternatively include more than three (e.g., four, five, six, etc.) telescoping tubes. Alternatively, telescoping sleeve 104 can include less than three (e.g., two) telescoping tubes.

As another example, while telescoping sleeve 104 has been described as resisting expansion and contraction as a result of frictional forces between the adjacent tubes of telescoping sleeve 104, other techniques can alternatively or additionally be used to provide resistance to expansion and contraction of telescoping sleeve 104. In some embodiments, for example, telescoping sleeve 104 includes one or more locking members that can be used to selectively prevent expansion and/or contraction of telescoping sleeve 104 during use. Telescoping sleeve 104 can, for example, include one or more thumb screws that can be tightened to inhibit the tubes of telescoping sleeve 104 from moving axially relative to one another. Alternatively or additionally, each of the tubes of telescoping sleeve 104 can include a spring loaded button arranged to cooperate with a recess or aperture formed in an adjacent tube of telescoping sleeve 104 to longitudinally fix the adjacent tubes relative to one another.

Telescoping sleeve 104 can alternatively or additionally include tapered sleeves that surround first, second, and third tubes 118, 120, 122. First and second tubes 118, 120 can, for example, have tapered sleeves extending around the outer surfaces of first and second tubes 118, 120 near the distal ends of first and second tubes 118, 120. Second and third tubes 120, 122 can also have tapered sleeves secured to the inner surfaces of second and third tubes 120, 122 near the proximal ends of second and third tubes 120, 122. When telescoping sleeve is expanded to a full extent, the outer tapered sleeves of first and second tubes 118, 120 can matingly engage the inner tapered sleeves of second and third tubes 120, 122 to prevent further expansion of telescoping sleeve 104.

As a further example, while inner layer 132 of first tube 118 of telescoping sleeve 104 has been described as including one or more lubricious materials, inner layer 132 can alternatively or additionally include other types of materials. In some embodiments, inner layer 132 includes one or more compressible materials, such as foams. In such embodiments, inner layer 132 can be configured to compress radially outwardly as catheter assembly 202 is disposed within first tube 118, which can help to create a fluid-tight seal between first tube 118 and outer sheath 208 of catheter assembly 202.

As another example, while first tube 118 of telescoping sleeve has been described as including inner layer 132 and outer layer 134, in some embodiments, first tube 118 of telescoping sleeve 104 includes only a single layer. The single layer can, for example, be formed of any of the materials that outer layer 132 has been described as including.

As an additional example, while the methods described above include inserting first tube 118 of telescoping sleeve 104 into Y-adaptor 102 prior to passing catheter assembly 202 through Y-adaptor 102, in certain embodiments, first tube 118 of telescoping sleeve 104 is inserted into Y-adaptor 102 after passing catheter assembly 202 through Y-adaptor 102.

In some embodiments, the proximal end of telescoping sleeve 104 can be attached (e.g., adhesively bonded, thermally bonded, welded, etc.) to the distal end of handle assembly 204. In such embodiments, catheter assembly 202 is first passed through Y-adaptor 102 and then, when catheter assembly 202 has been guided a sufficient distance into the blood vessel of the patient, first tube 118 of telescoping sleeve 104 is inserted into Y-adaptor 102 and valve 110 is tightened around first tube 118 to create a substantially fluid-tight seal. Telescoping sleeve 104 can, for example, be expanded prior to inserting first tube 118 into Y-adaptor 102.

Figure 6:
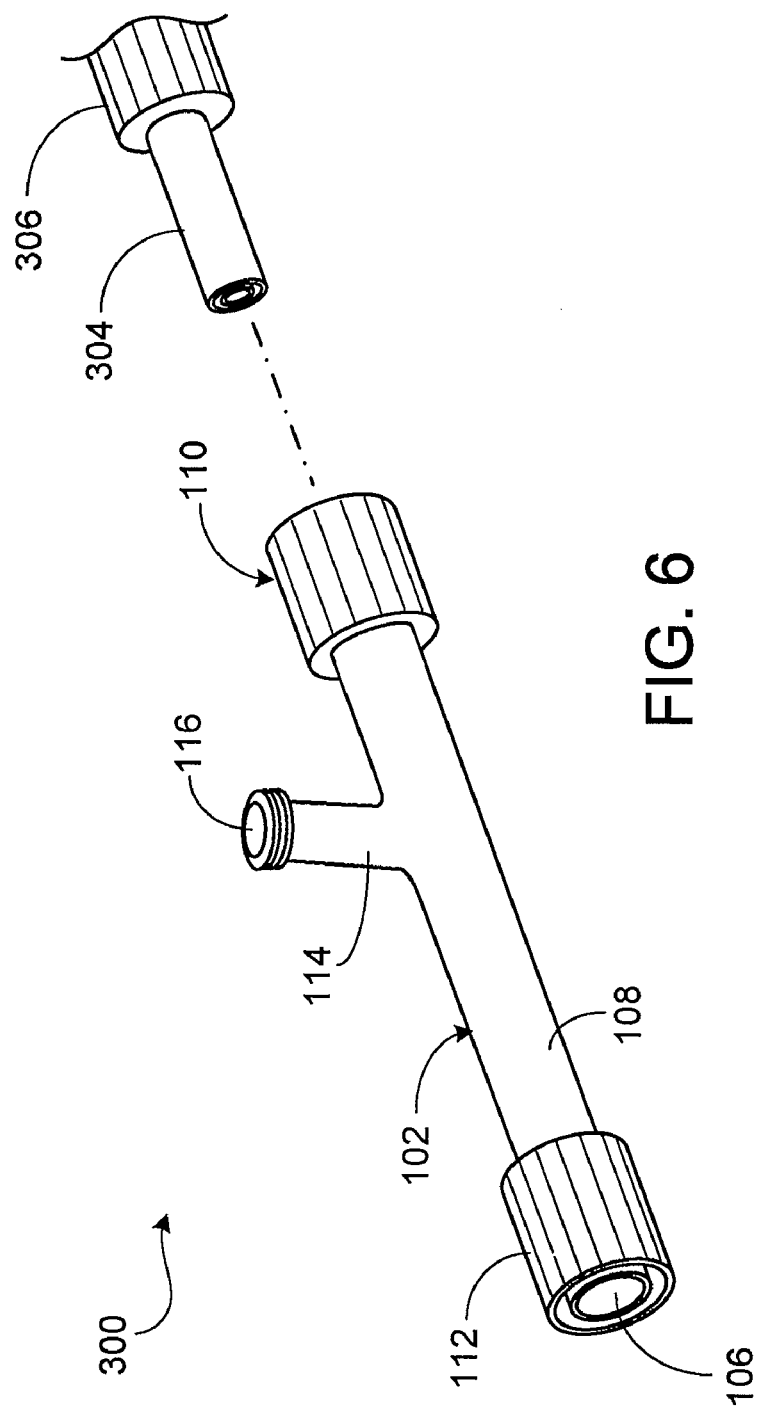
FIG. 6 is a perspective, partially exploded view of an adaptor system including a non-telescoping sleeve.

As a further example, while adaptor system 100 has been described as including telescoping sleeve 104, a non-telescoping sleeve can alternatively or additionally be used. Referring to FIG. 6, for example, an adaptor system 300 includes Y-adaptor 102 and a sleeve 304 configured to be disposed within valve 110 of Y-adaptor 102. Sleeve 304 includes a knurled portion 306 on its proximal end that allows the user to more easily grasp sleeve 304 during use. The outer diameter of knurled portion 306 is greater than the outer diameter of the remainder of sleeve 304.

Figure 7:
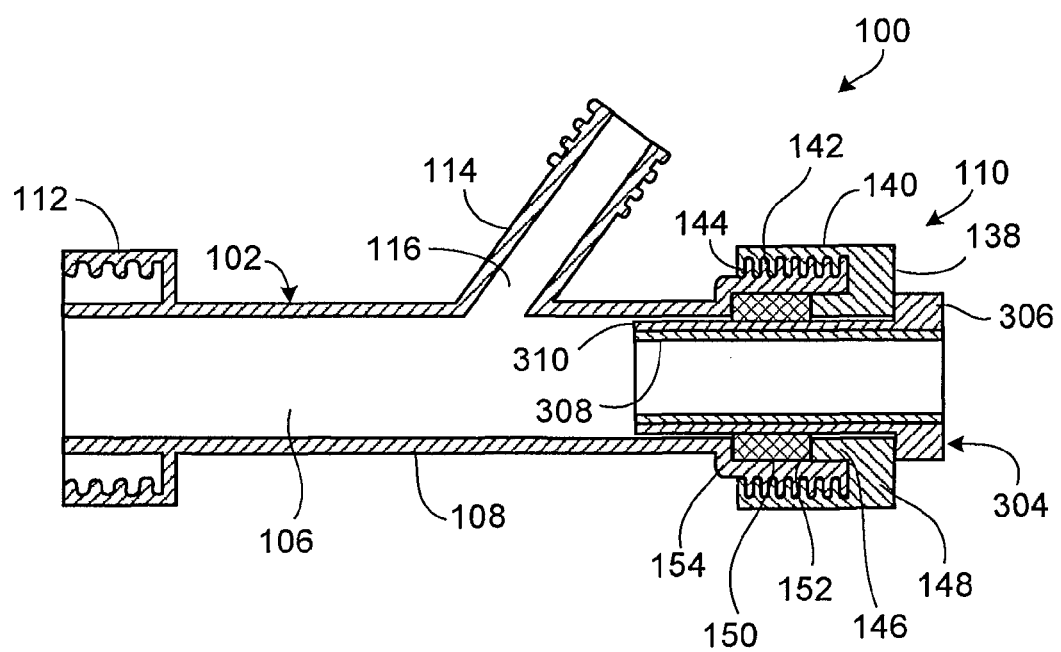
FIG. 7 is a cross-sectional view of the adaptor system of FIG. 6 in a sealed configuration.

When sleeve 304 is fully inserted into Y-adaptor 102, as shown in FIG. 7, knurled portion 306 abuts proximal end 138 of valve 110, preventing further distal movement of sleeve 304 into Y-adaptor 102. Valve 110 is tightened around sleeve 304 in a manner similar to that described above in order to provide a substantially fluid-tight seal between the inner surface of O-ring 150 and the outer surface of sleeve 304. Sleeve 304 includes an inner lubricious layer 308 and a rigid outer layer 310. Inner and outer layers 308, 310 of sleeve 304 can include any of the various materials described above with respect to inner and outer layers 132, 134 of first tube 118 of telescoping sleeve 104. As an alternative to including inner and outer layers 308, 310, sleeve 304 can include a single layer. The single layer can, for example, include one or more of the rigid materials described above with respect to inner tube 118 of telescoping sleeve 104. Adaptor system 300 can be used in a manner similar to that of adaptor system 100 described above.

Figure 8:
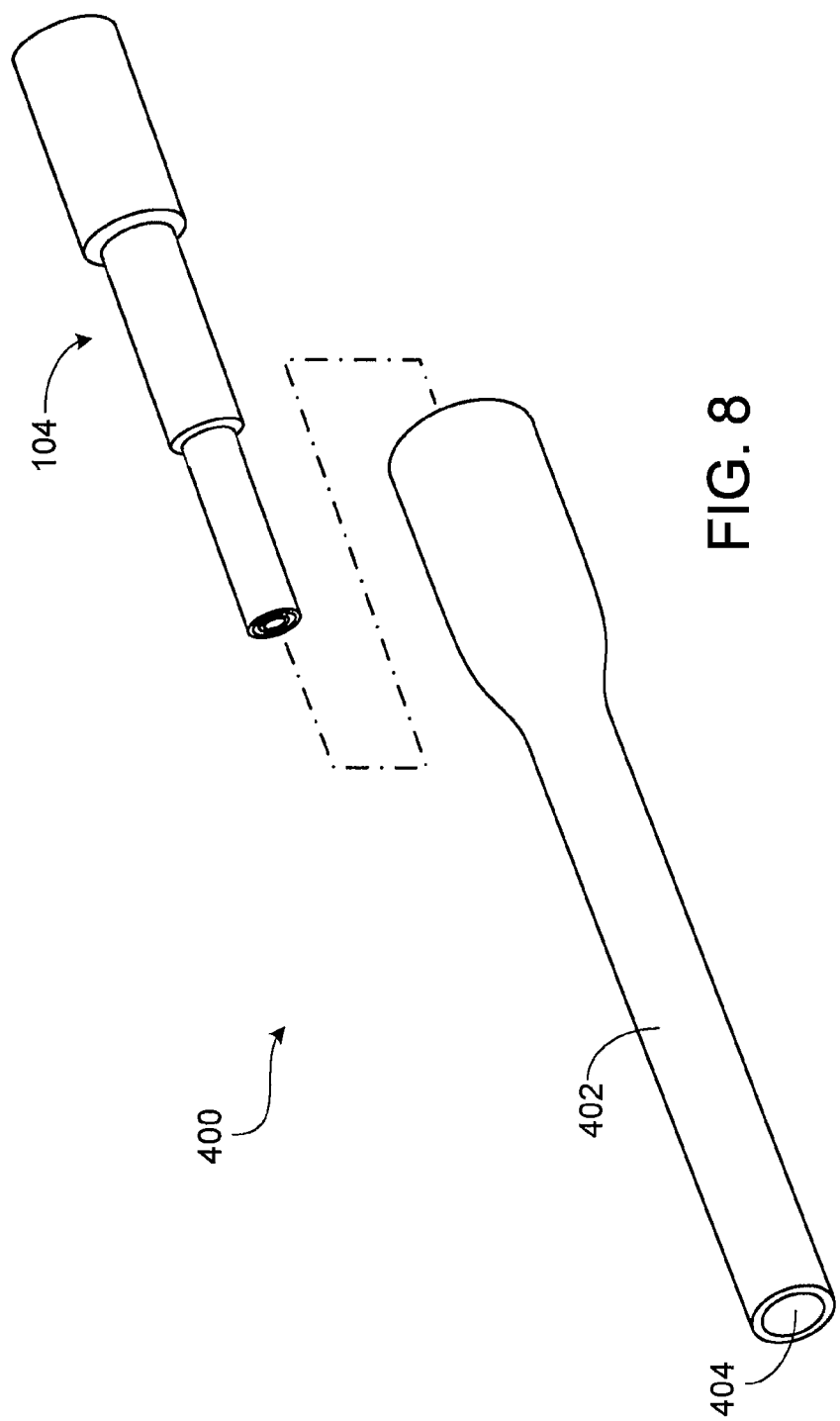
FIG. 8 is a perspective, partially exploded view of a system including an introducer sheath and a non-telescoping sleeve.
Figure 9:
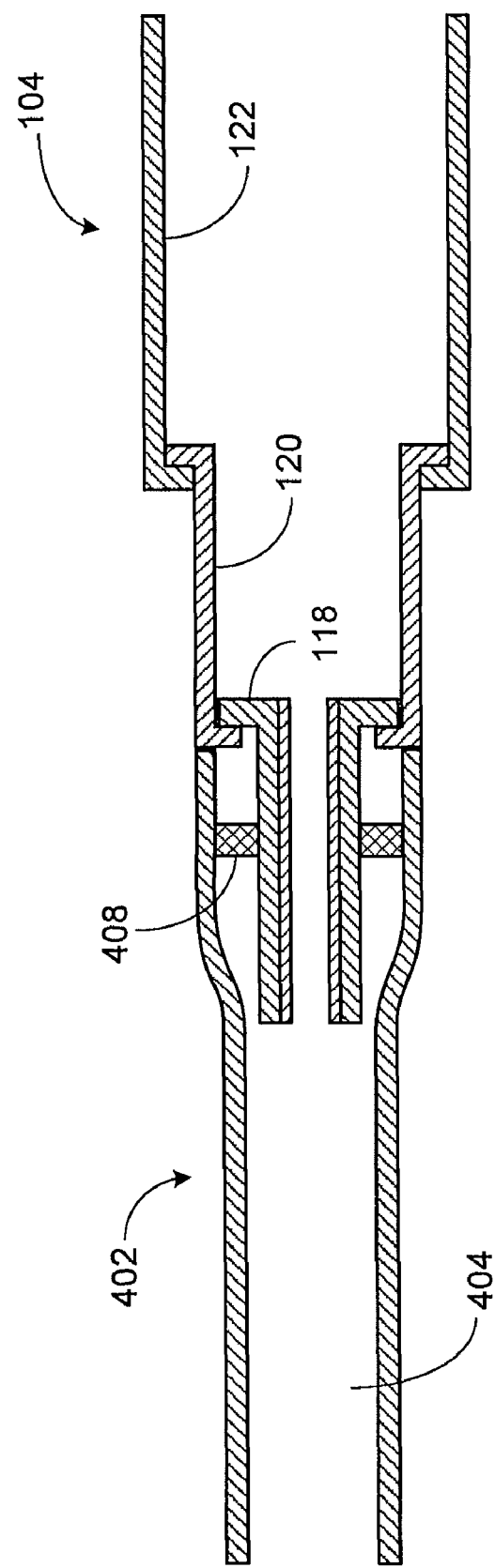
FIG. 9 is a cross-sectional view of the system of FIG. 8 in a sealed configuration.

As another example, while embodiments above describe using sleeves 104, 304 in combination with Y-adaptor 102 and guide catheter 250, sleeves 104, 304 can alternatively or additionally be used in combination with an introducer sheath. Referring to FIG. 8, for example, a system 400 includes an introducer sheath 402 and telescoping sleeve 104. As shown in FIG. 9, introducer sheath 402 includes a lumen 404 extending therethrough and a seal 408 disposed within lumen 404 near a proximal end of introducer sheath 402. First tube 118 of telescoping sleeve 104 is disposed within seal 408 of introducer sheath 402. Seal 408 is configured so that, with first tube 118 of telescoping sleeve 104 disposed within seal 408, a fluid-tight seal is created between the inner surface of seal 408 and the outer surface of first tube 118. Seal 408 can, for example, include a resilient disk with a crossed slit extending through the seal along its central axis such that when first tube 118 is inserted within the slit, the slit expands to create the fluid-tight seal between seal 408 and first tube 118. Alternatively, seal 408 can include a resilient O-ring having a lumen with a diameter (in an undeformed configuration) that is equal to or slightly less than the outer diameter of first tube 118.

System 400 can be used in a manner similar to that described above with respect to the combination of adaptor system 100 and guide catheter 250. For example, introducer sheath 402 can be inserted into a blood vessel of a patient and catheter assembly 202 of stent delivery system 200 (shown in FIG. 4) can be inserted into the blood vessel via introducer sheath 402. The fluid tight seals between seal 408 and first tube 118 of telescoping sleeve 104 and between outer sheath 206 of catheter assembly 202 and first tube 118 of telescoping sleeve 104 can inhibit blood from leaking through the proximal end of introducer sheath 402 during use. The stent-carrying portion of catheter assembly 202 can be positioned within an occluded region of the blood vessel and outer sheath 206 can be retracted to deploy stent 216 within the occluded region of the blood vessel. As discussed above, inner lubricious layer 132 of first tube 118 of telescoping sleeve 104 helps to reduce frictional forces between outer sheath 206 and first tube 118 when outer sheath 206 is retracted to deploy stent 216, which can improve the accuracy with which stent 216 is deployed within the blood vessel. In addition, during use, telescoping sleeve 104 can be expanded such that the proximal end of telescoping sleeve 104 abuts the distal end of handle assembly 204 of stent delivery system 200 to inhibit catheter assembly 202 from bowing outward and to inhibit unintended distal movement of handle assembly 204 during use. As discussed above, this can further improve the accuracy with which stent 216 is deployed within the blood vessel.

While introducer sheath 402 of system 400 has been described as being used with telescoping sleeve 104, introducer sheath 402 can alternatively or additionally be used with a non-telescoping sleeve, such as sleeve 304.

As another example, while systems 100, 300, 400 have been described as being used with stent delivery system 200, which includes rotatable knob 226 and pull grip 222 to retract outer sheath 206 and deploy stent 216, any of various other types of stent delivery systems that include a retractable sheath can alternatively or additionally be used with systems 100, 300, 400. Moreover, while systems 100, 300, 400 have been described as being used with stent delivery systems, any of various other types of medical systems that include retractable sheaths can be used with the systems described herein. Examples of other types of medical systems with retractable sheaths include systems configured to deliver balloon expandable stents, stent-grafts, filters, and coils. In addition, systems 100, 300, and 400 can be used with medical systems including catheters that do not include a retractable sheath.

As another example, while systems 100, 200, 300, 400 have been described as being used in various different types of blood vessels, they can alternatively or additionally be used in other types of body vessels.

Other embodiments are in the claims.

What is claimed is:

1. A system, comprising:
    an adaptor being configured to be secured to a guide catheter, the adaptor including a housing defining a lumen configured to receive a portion of a catheter assembly comprising an inner member at least partially surrounded by an outer sheath; and
    wherein a valve is secured to a proximal end region of the housing,
    a sleeve configured to be disposed between the outer sheath of the catheter assembly and the adaptor when the catheter assembly is disposed in the lumen of the adaptor,
    wherein the sleeve includes a first tube, a second tube, and a third tube,
    wherein the sleeve is a telescoping sleeve such that the first tube is configured to slide within the second tube and the second tube is configured to slide within the third tube,
    wherein the first tube is secured to the adaptor with the valve.

2. The system of claim 1, wherein the sleeve is formed of one or more materials having a tensile strength of at least about 63 MPa, and the sleeve has a wall thickness of at least about 0.002 inch.

3. The system of claim 1, wherein a distal portion of the sleeve is configured to be disposed between the outer sheath of the catheter assembly and the adaptor, and a proximal portion of the sleeve is configured to be positioned proximal to the adaptor.

4. The system of claim 3, wherein the proximal portion of the sleeve has a first outer diameter and the distal portion of the sleeve has a second outer diameter, the first outer diameter being greater than the second outer diameter.

5. The system of claim 1, wherein the sleeve is configured to extend from the adaptor to a distal end of a handle to which the inner member of the catheter assembly is secured.

6. The system of claim 1, wherein the valve can be tightened around the first tube.

7. The system of claim 6, wherein the sleeve is configured so that a friction level between the first tube and the outer sheath of the catheter assembly remains substantially constant as the valve is tightened around the sleeve.

8. The system of claim 1, wherein the sleeve comprises one or more materials having a tensile strength of at least about 63 MPa.

9. The system of claim 1, wherein the sleeve comprises one or more metals.

10. The system of claim 1, wherein the sleeve comprises an inner layer and an outer layer, the inner layer having a coefficient of friction of about 0.25 or less.

11. The system of claim 10, wherein the inner layer comprises silicone.

12. The system of claim 1, wherein the sleeve has an inner diameter and the outer sheath of the catheter assembly has an outer diameter, the inner diameter of the sleeve being no greater than about 0.003 inch greater than the outer diameter of the outer sheath of the catheter assembly.

13. The system of claim 1, further comprising a guide catheter secured to the adaptor.

14. A system, comprising:
    an adaptor including a housing and a valve secured to a proximal end region of the housing; and
    a sleeve defining a lumen, the sleeve being configured to be disposed within the valve so that a substantially liquid-tight seal can be created between the valve and the sleeve, the sleeve being configured so that a catheter assembly comprising an inner tubular member and an outer tubular member at least partially surrounding the inner tubular member can be disposed within the lumen of the sleeve,
    wherein the sleeve comprises an inner layer and an outer layer, the inner layer having a coefficient of friction of about 0.25 or less,
    wherein the sleeve includes a first tube secured to the valve, a second tube, and a third tube,
    wherein the sleeve is a telescoping sleeve such that the first tube is configured to slide within the second tube and the second tube is configured to slide within the third tube.

15. The system of claim 14, wherein the inner layer of the sleeve comprises silicone.

16. The system of claim 14, wherein the outer layer is formed of one or more materials having a tensile strength of at least about 63 MPa.

17. The system of claim 14, wherein the outer layer of the sleeve comprises one or more metals.

18. The system of claim 14, wherein the sleeve has an inner diameter and the outer sheath of the catheter assembly has an outer diameter, the inner diameter of the sleeve being no greater than about 0.003 inch greater than the outer diameter of the outer sheath of the catheter assembly.

19. The system of claim 14, wherein the valve comprises a resilient o-ring.

20. The system of claim 14, wherein the valve is a Touhy Borst valve.

21. The system of claim 14, wherein the sleeve is substantially radially incompressible.

22. The system of claim 14, wherein the adaptor is configured to be secured to a guide catheter.

23. The system of claim 14, further comprising an introducer sheath, the valve being disposed within the introducer sheath.

24. The system of claim 23, wherein the valve is a membrane disposed within the introducer sheath, the membrane having intersecting slits through which a catheter assembly can be inserted.

25. The system of claim 23, wherein a distal portion of the sleeve is configured to be disposed between the outer sheath of the catheter assembly and the valve, and a proximal portion of the sleeve is configured to be positioned proximal to the introducer sheath.

26. The system of claim 25, wherein the proximal portion of the sleeve has a first outer diameter and the distal portion of the sleeve has a second outer diameter, the first outer diameter being greater than the second outer diameter.

27. The system of claim 23, wherein the sleeve is configured to extend from the introducer sheath to a distal end of a handle to which the inner member of the catheter assembly is secured.

* * * * *